United States Patent [19]

Sommer

[11] Patent Number: 4,950,073

[45] Date of Patent: Aug. 21, 1990

[54] SUBMICRON PARTICLE COUNTING ENLARGING THE PARTICLES IN A CONDENSATION BASED GROWTH PROCESS

[75] Inventor: Holger T. Sommer, Greenbelt, Md.

[73] Assignee: Pacific Scientific Company, Newport Beach, Calif.

[21] Appl. No.: 308,556

[22] Filed: Feb. 10, 1989

[51] Int. Cl.$^5$ .............................................. G01N 1/00

[52] U.S. Cl. ...................................................... 356/37

[58] Field of Search ................... 73/865.5, 28; 356/37, 356/335–337, 438

[56] References Cited

U.S. PATENT DOCUMENTS

| | | | |
|---|---|---|---|
| 3,462,609 | 8/1969 | Beattie | 356/37 |
| 3,694,085 | 9/1972 | Rich | 356/37 |
| 3,806,248 | 4/1984 | Sinclair | 356/37 |
| 4,449,816 | 5/1984 | Koshaka et al. | 365/37 |
| 4,790,650 | 12/1988 | Feady | 356/37 |
| 4,792,199 | 12/1988 | Borden | 356/37 |
| 4,794,789 | 6/1989 | Natako | 73/865.5 |

FOREIGN PATENT DOCUMENTS

| | | | |
|---|---|---|---|
| 1206658 | 1/1986 | U.S.S.R. | 356/37 |

OTHER PUBLICATIONS

Nesti, Jr., "The Condensation Nuclei Counter as an Air Pollution Weapon", No date.

*Primary Examiner*—Robert Raevis
*Attorney, Agent, or Firm*—Lane, Aitken & McCann

[57] ABSTRACT

An apparatus for detecting submicron particles in air includes a saturator for saturating a sample stream of the air with a vapor of a low volatility liquid and a condenser for cooling the vapor to form droplets around the particles to result in particles of a size detectable by an optical detector. Conduits extend through a bath of the liquid in the saturator so that sample streams passing through the conduits are heated by the bath. A flow divider divides a single sample stream at the inlet of the saturator into a plurality of laminar flow streams corresponding in number to the conduits. The condenser is a heat exchanger having a plurality of tubes with funnel-shaped inlet ends positioned over the bath of the saturator, and the tubes are inclined toward their inlet end so that condensed vapor flows back into the bath. A method for detecting particles in various size ranges involves operating the saturator at different temperatures to vary the minimum size particle which can be grown by condensation to a detectable size.

6 Claims, 2 Drawing Sheets

SUBMICRON PARTICLE COUNTING ENLARGING THE PARTICLES IN A CONDENSATION BASED GROWTH PROCESS

BACKGROUND OF THE INVENTION

The present invention relates to the measurement of concentrations of particles in air and, more particularly, to an apparatus and method for detecting particles of submicron size.

A major characteristic in the development of the microelectronic industry is the reduction in size of manufactured components. Each new generation of products requires higher standards for the "clean rooms" in which the products are made in order to keep the percentage of defective products to an economically acceptable level. For a 0.5 micrometer component, the presence of a 0.1 micrometer impurity is "killing", and a 0.01 micrometer particle is enough to alter the behavior of a dielectric film having a 0.02 micrometer diameter.

Atmospheric air contains high concentrations of particles having diameters less than 0.1 micrometers. Although the filters used for air-conditioning clean rooms are highly effective in removing these ultrafine particles, when a mishap occurs in the manufacturing process, it can be expected that a non-negligible fraction of ultrafine particles remains in the atmosphere of the clean room. However, the most likely sources of such particles involve the manufacturing techniques themselves (gas-phase reactions, atomization of fluids, corona discharge, degassing of solids, abrasion, and the like). The current goal in contamination control is to measure very low concentrations, on the order of a few particles per cubic meter, of particles ranging in size from 0.01 micrometers to 10 micrometers. Monitoring must be performed in real time in order to allow rapid intervention in case contamination of the air should occur.

The measurement of contamination in clean rooms has been carried out using optical counters in which a focused light beam constitutes an optical cell which the particles in the air cross one by one. The light scattered individually by each particle is collected by a photosensitive detector. The resultant electrical signals are stored in a multichannel analyzer and the particle size distribution of the sampled aerosol is deduced. Such optical counters using a white light source can be used for particles ranging in size from 0.3 or 0.5 micrometers to approximately 10 micrometers to sample the air at rates of 0.1 or 1 cubic feet per minute, depending on the model of optical counter used. Optical counters employing lasers can be used for detecting particles as small as 0.1 micrometers. Thus, it can be appreciated that further development has been necessary in order to detect particles in the range of 0.01 micrometers to 0.1 micrometers.

It has been known to use the particles as nuclei for the condensation of a supersaturated vapor in an expansion chamber and then to detect with an optical cell the resulting droplets, which are of substantially greater size than the particles alone. However, in one such known device, the expansion chamber in which the droplet formation occurs is combined with the optical cell and, therefore, the measurement relates to the attenuation of the light beam of the optical cell by the cloud of droplets formed. The use of this type of instrument is, thus, limited to concentrations greater than approximately 100 particles per cubic centimeter. In another device employing the particles as condensation nuclei, the droplets formed can be counted individually, with detection being carried out in the same way as in optical counters. However, the sampling rate of the device is very low, approximately 0.3 liters/minute, so that when concentrations of a few particles per cubic meter are involved, sampling times are extremely long.

SUMMARY OF THE INVENTION

By the present invention, an apparatus and method is provided by which particles as small as 0.001 micrometers can be detected by an optical counter for volumes of air sampled at a rate of as much as one cubic foot per minute. A stream of the sample of air containing the particles is fed under low pressure in laminar flow into a flow divider which divides the stream into a plurality of streams having equal flow rates and maintains laminar flow. The flow rates in the plural sample streams are maintained equal, in part, by recombining channels in the flow divider which transmit to other streams any excess pressure in one of the streams. The sample streams flow through conduits extending through a bath of liquid maintained at a temperature above room temperature in a saturator, so that the streams are heated by the bath. The conduits terminate above the surface of the liquid and direct the sample streams back through a space over the surface of the liquid, which is a low volatility liquid, so that the sample becomes saturated with the vapor rising from the bath. The sample saturated with the vapor flows from the saturator into a condenser where the mixture is cooled so that the air becomes supersaturated and the vapor condenses on the condensor walls and particles in the sample stream, forming a droplet around each particle having at least a predetermined minimum size and thereby effectively increasing the size of the particles so that they can be detected by an optical counter. The condenser is a heat exchanger in which the vapor saturated air passes through a plurality of tubes after entering the tubes through streamlined inlets. Water is circulated in the condenser around the tubes to lower the temperature of the air sample to slightly below room temperature. The tubes are inclined toward their inlets so that any vapor which condenses on the walls of the tubes will drip back into the bath of the saturator. Outlets of the tubes direct the flow into a cone, which combines the streams from the tubes and feeds them to the chamber of an optical particle counter used as a signal pulse counter and not as a spectrophotometer.

By varying the temperature of the saturator, more specifically, the temperature of the liquid bath, the size of particles which can be grown to a detectable size is controlled. As a result, a technique is provided for detecting and counting particles in different size ranges.

DETAILED DESCRIPTION OF THE PREFERRED EMBODIMENT

Figure 1:
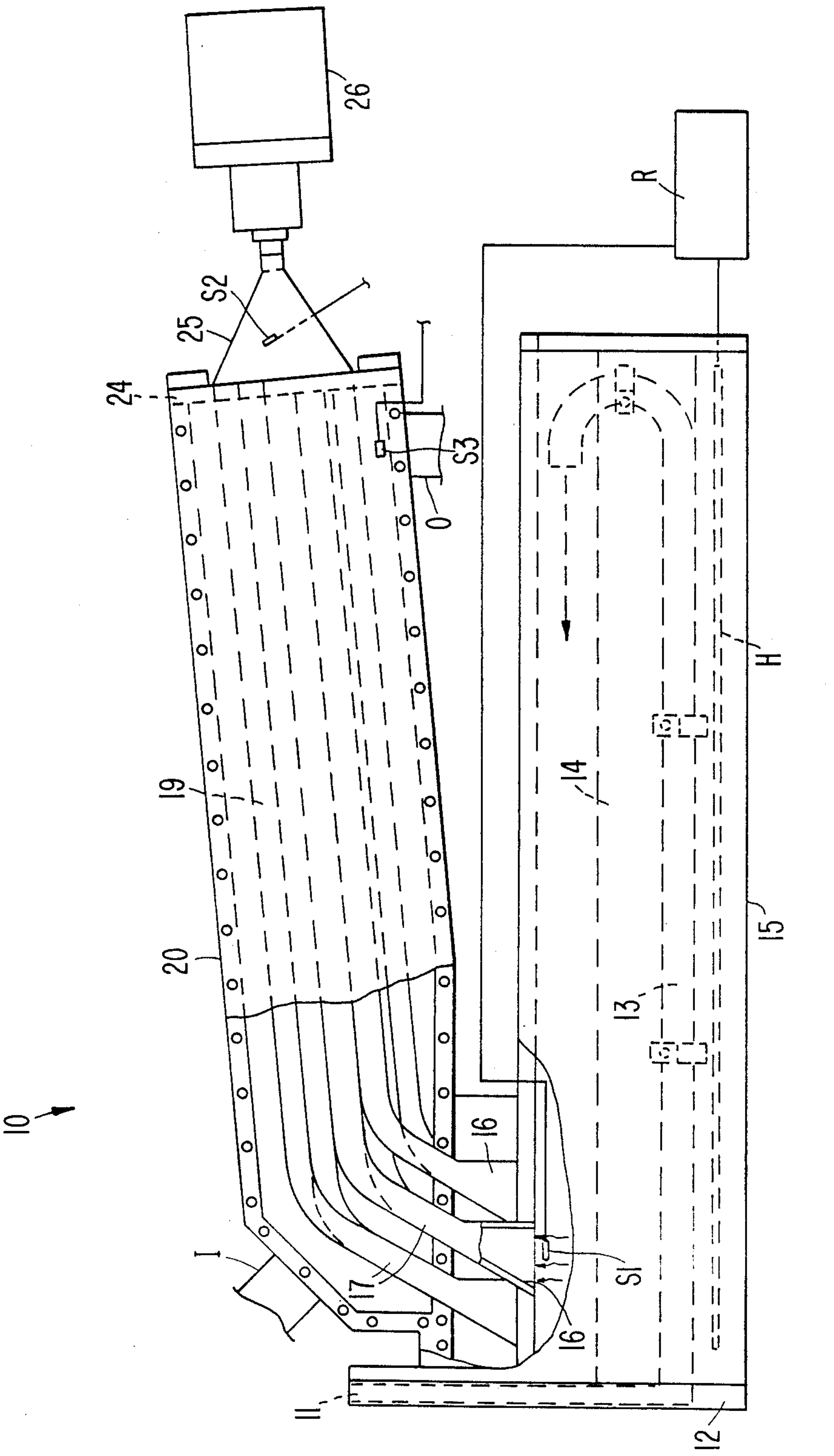
FIG. 1 is a schematic view, with parts broken away, of the submicron particle counting system according to the present invention.

As can be seen from FIG. 1, the apparatus according to the present invention for detecting and counting submicron particles, which is designated generally by the reference numeral 10, defines a flow path for a sample stream of air in order to determine the number and size of the extremely small particles in the air. The sample stream of air enters the apparatus 10 at 1 cu.ft./min. flow rate, drawn by pressure just slightly below atmospheric through an inlet channel 11 of a flow divider 12. The inlet channel 11 divides into a plurality of channels connecting with conduits 13 extending through a bath of a liquid 14 of low volatility in a container defining the saturator 15 of the apparatus 10. The conduits 13 extend parallel to one another from one end of the saturator 15, where the flow divider 12 is positioned, to the end of the saturator 15 distal to the inlet channel 11, where the conduits curve about 180 degrees upwardly and back toward the inlet channel 11. The conduits 13 terminate near the distal end, where their outlet ends define outlet openings having axes parallel to the surface of the bath of liquid 14. The outlet openings direct the streams of the air sample through a space above the bath of liquid 14, which is saturated with the vapor of the liquid. A preferred low volatility liquid for the bath is glycerol, which make it possible to detect smaller particles than other liquids.

The sample streams traveling through the conduits 13 are heated by heat exchange with the liquid in the bath 14 and, when the streams pass through the space above the bath, they become saturated with the vapor rising from the liquid. The temperature of the sample should approximate the temperature of the conduits 13 by the time it flows into the space over the bath of liquid 14, and the vapor pressure should approach the saturating value at that temperature. The heating of the sample in the tubes 13 permits the sample to become saturated more easily over the bath of the liquid 14. A known temperature regulator R of the "constant temperature" type, rather than the "constant energy flux type", having a precision of 1% is used to adjust the temperature of the saturator 15 to any of a range of predetermined desired temperatures and maintain it there. The temperature regulator R includes an electric resistance heating element H and at least one sensor S1 positioned where the saturated sample enters the condenser 20, so that the temperature of the bath of liquid 14 can be controlled in response to the temperature of the saturated sample leaving the saturator 15. Other heating elements (not shown) are provided in the bath of liquid 14 to initially bring the saturator 15 up to its operating temperature. A filling inlet and a draining outlet (not shown) are provided in the saturator 20, and a viewing window may be included to check the level of the bath of liquid 14.

The air sample saturated with the vapor flows into the inlets 16 of tubes 19 of a heat exchanger defining the condenser 20 for the apparatus 10, the inlets 16 being positioned over the saturator 15, and the sensor or sensors S1 being positioned at the inlets 16. Water is circulated around the tubes 19 in the condenser 20 from an inlet I to an outlet O, which causes the air-vapor mixture within the tubes 19 to become supersaturated and condense around the particles in the mixture which have at least a predetermined minimum size. The resulting droplets are considerably larger in size that the bare particles, and the apparatus 10 thereby effectively increases the size of the particles enough so that they can be detected by an optical counter. Outlet ends of the tubes 19 transmit the sample to a conical reducing member 25, which leads to the chamber of a particle detector 26. The particle detector 26 is immediately downstream of the condenser 20 so that the droplets do not evaporate before they are detected. Droplet stability is assured by the use of the liquid of suitable volatility.

A preferred temperature for the sample as it exits the condenser 20 is about 15 degrees C. This temperature, which is below room temperature, assures that remaining vapor will not condenser on the conical reducing member 25 and the particle detector 26. A sensor S2 is provided in the conical reducing member 25 to sense the temperature of the sample. The sensed temperature is sent to a controller for a source of chilled water for the condenser 20, whereby the temperature and flow rate of the chilled water flowing through the condenser can be adjusted. A temperature sensor S3 is positioned at the outlet O of the condenser 15 to monitor the temperature of the exiting water.

The inlet channel 11 for the sample stream of air is divided into a plurality of streams so that efficient heat transfer can take place between the bath of liquid 14 and the sample in the saturator 15. It is important to maintain an equal flow of the sample through each of the conduits 13 to prevent the count of particles from losing its accuracy. If one or more of the streams of the sample flows at a faster or slower rate through its conduit 13 than the other streams flow through their conduits, the subject stream will be heated less or more than the other streams, and the minimum size particle in the subject stream which can be grown to a size detectable in an optical counter will be different from the minimum size particles in the other streams which can be grown to detectable size.

Figure 2:
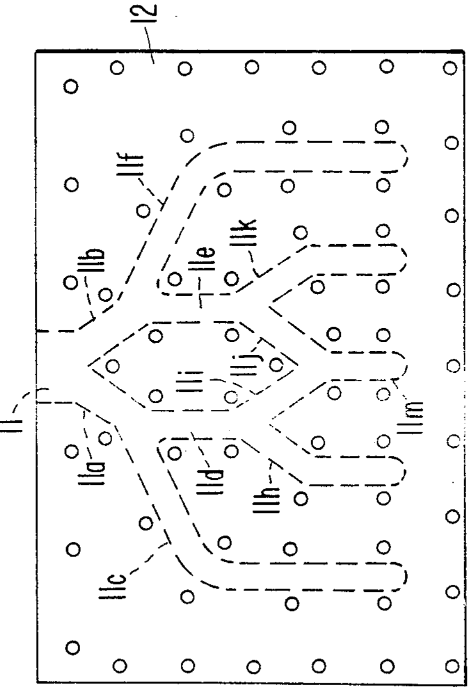
FIG. 2 is a left-end view of the saturator in the apparatus of FIG. 1, showing the dividing and recombining of the sample stream entering the saturator.

The inlet channel 11 is divided into a plurality of smaller channels and then partially recombined in order to assure an equal flow of the sample through each of the conduits 13. As can be seen from FIG. 2, which shows the inlet channel 11 at the entrance to the saturator 15, the inlet channel 11 is divided into two channels 11*a* and 11*b* of equal cross-section, which further divide into channels 11*c*–11*f*. The channels 11*d* and 11*e* divide into four channels 11*h*–11*k*, and the channels 11*i* and 11*j* combine back together to form a middle channel 11*m*. Each channel divides into two further channels at a time, so that the introduction of the turbulence is avoided, and laminar flow is maintained. Turbulence can cause some of the submicron particles in the sample to rub off on the surfaces of the channels 11 or the conduits, thereby affecting the accuracy of the measurement. Furthermore, turbulence in the saturator 15 can result in "self nucleation", which is the formation of detectable droplets without the presence of particles. Such turbulence can also cause detectable droplets to be formed around particles smaller than the expected minimum size, also affecting the accuracy of the count.

The channels 11*c*, 11*h*, 11*m*, 11*k* and 11*f* connect with the conduits 13. The recombining channels 11*i* and 11*j* provide a pneumatic feedback, so that if the pressure in the middle channel 11*m* becomes large, which would cause a greater rate of flow through the middle channel, the pressure is transmitted back through the channels 11*i* and 11*j* to increase the flow rates in the channels 11*h* and 11*k*. Similarly, if the pressure in either channel 11*h* or 11*k* becomes larger than the pressure in the other and larger than the pressure in the middle channel 11*m*, the pressure is transmitted back to the middle channel **11*m* and the other channel through the channels 11*i* and 11*j*. The channels 11*c*, 11*h*, 11*m*, 11*k* and 11*f* should all be the same cross-sectional area, and the channels 11*i* and 11*j* should be one-half of this area. The cross-sectional area of channels 11*d* and 11*e* should be 1.5 times the area of the channels which connect with the conduits 13. These relative sizes help provide equal flow in the sample streams entering the conduits 13**.

Figure 3:
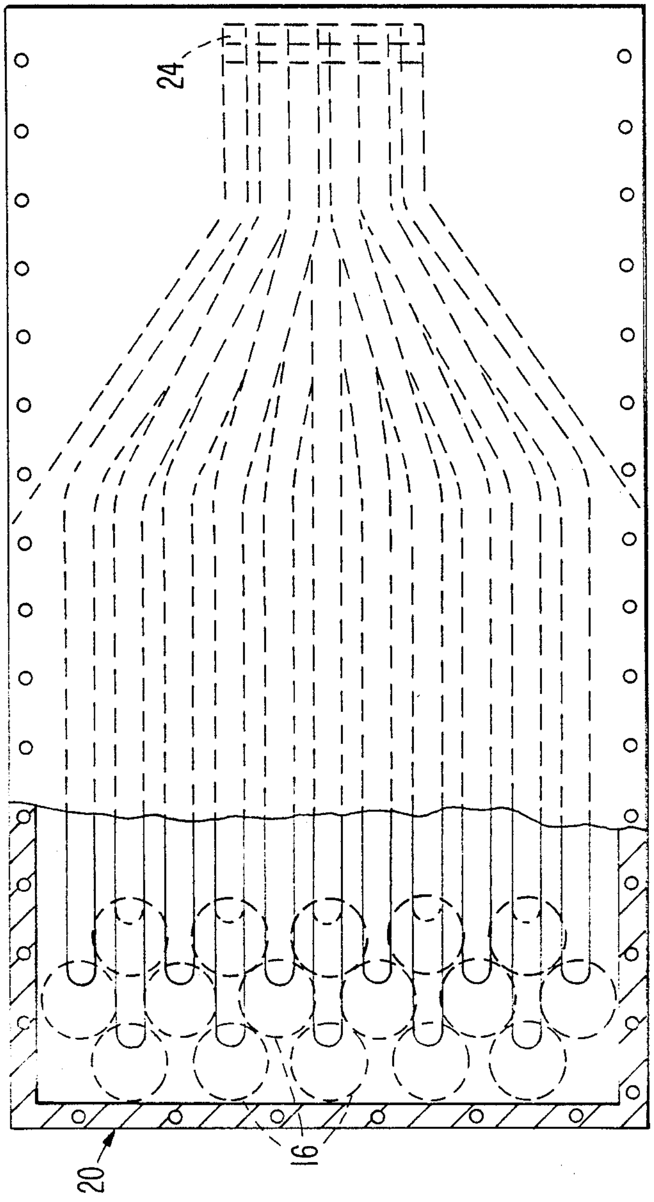
FIG. 3 is a plan view, with a portion broken away, of the condenser of the apparatus of FIG. 1.
Figure 4:
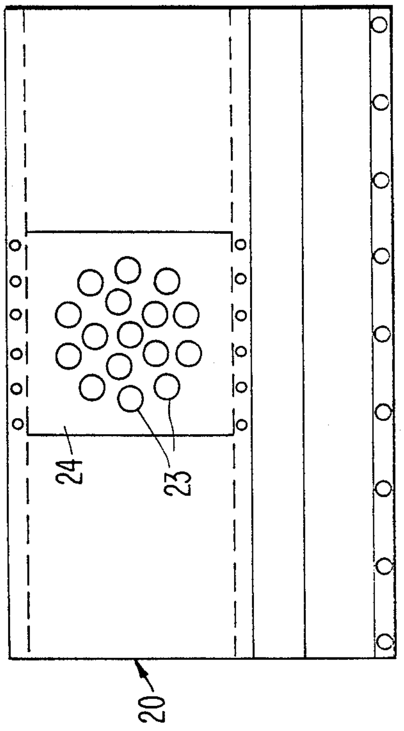
FIG. 4 is a right-hand view of the condenser of FIG. 3.

As can best be seen from FIGS. 1 and 3, the inlets 16 of the tubes 19 are funnels which are generally vertically oriented to permit the mixture of the sample stream and the saturated vapor to flow from the saturator 15 into the tubes 19. The funnels are frustums of circular cones wherein the cones have oblique axes. By this shape, one side of each funnel defines a straight line with one side of an inlet portion 17 of its associated condenser tube 19, the funnels are coaxial with the inlet portions 17, and the flow of the saturated sample from the saturator 15 enters the tubes 19 in a more streamlined manner. The streamlined shape prevents turbulence of the saturated sample in the tubes 19 of the condenser 20, which could cause the droplets, with their particle nuclei, to attach to the walls of the tubes 19 and drain back into the saturator 15. The streamlined shape also permits the bends in the condenser tubes 19 to be accomplished in a small space. The funnels are arranged in a grouped pattern at an inlet end of the condenser 20, and the tubes 19 extend longitudinally of the condenser 20 parallel to one another in a generally rectangular array. As the tubes 19 approach the outlet end of the condenser 20, which is distal to the inlets 16, the tubes are bent into a more closely grouped circular pattern. The outlet ends of the tubes 19 in the circular pattern are connected to openings 23 in a member 24 at the outlet end of the condenser 20, where the tubes 19 are in fluid communication with the inlet end of a reducing member 25, which is conical in nature to permit the transition from the plurality of tubes 19 to the particle detector 26.

The condenser 20 cools the mixture in the tubes 20 to below room temperature, and the cooling is accomplished slowly enough that self-nucleation of droplets where there are no particles and nucleation around particles too small are avoided. Although heat exchange must be promoted, the transfer of vapor to the walls of the tubes 19 should be minimized. The tubes 19 are inclined toward their inlets 16, the inlets 16 being the lowest portions of the tubes 19, so that any of the vapor which condenses on the walls of the tubes to liquid flows back through the inlets 16 of the tubes and into the bath of liquid 14 in the saturator 15. In order to provide the inclination of the tubes 19 in the illustrated embodiment, much of the casing of the condenser 20 extends at an inclination to the horizontal.

Typically, the particle detector 26 is an optical detector comprising a detection chamber, a light source in the form of a focused light beam, for example a He-Ne laser beam, or semi-conductor laser diode beam, which the sampled particles cross one by one, and a photosensitive detector which collects the light scattered individually by each particle. Another type of particle detector can be used in which light from the source is partially extinguished or occluded by particles, and a photosensitive detector is provided which detects the partial extinction or occlusion of light individually by each particle. The particles must be at least a predetermined threshold size before they will vary, that is, scatter or extinguish, the light by a detectable amount.

Depending on other elements and conditions in the apparatus 10, when the saturator 15, more specifically the liquid bath, is maintained at a temperature of, for example, 90 degrees C., particles as small as 1 nanometer (0.001 micrometer) in diameter will grow to a detectable size. By maintaining the saturator 15 at lower temperatures, while all of the other factors are the same, droplets will not form around particles quite as small as 1 nanometer, and a larger minimum size of particle is needed to cause detection. Thus, by operating at different temperatures and knowing the minimum size particle which can be grown to detectable size at the known temperature, the particles for different size ranges can be counted. In order to obtain the count of particles in the size range, for example, from 0.1 to 0.01 micrometers, the saturator 15 can be maintained at a temperature at which only those particles of 0.01 micrometers and more are grown to a detectable size. Then, a known other type of instrument is used to measure the particles having a size of 0.1 micrometers and more. The count of particles obtained by the other type of instrument is substrated from the count of particles above 0.1 micrometers detected by the apparatus according to the present invention to determine the number of particles in the range of 0.01 to 0.1 micrometers. If it is desired to obtain the number of particles in the range of 0.001 to 0.01 micrometers, the saturator is additionally maintained at a temperature at which all particles above 0.001 micrometers are grown to a detectable size. Then the count of the other instrument and the count of the present apparatus when the temperature of the saturator 15 permits only particles having a size greater than 0.01 micrometers to become detactable are added together and substracted from the count obtained by the present apparatus when the saturator is maintained at a temperature in which particles having a size greater than 0.001 micrometers become detectable.

The temperature at which the saturator 15 is maintained must not be too high in order to avoid destruction of the droplets to be measured. Ammonium sulfate particles, for example, are destroyed at 96 degrees C. In addition, the temperature of the sample at the outlet of the condenser 20 should be within the usable range for optical counters (5–55 degrees C. for most instruments). The temperature of the tubes 19 of the condenser 20 is maintained close to room temperature, and only the temperature of the saturator 15 is varied.

Although a preferred embodiment of the apparatus and method according to the present invention has been described herein, it is understood that the invention is not limited to such an embodiment, but that a latitude of modification, change, and substitution is intended. Accordingly, it is appropriate that the appended claims be construed broadly and in a manner consistent with the spirit and scope of the invention disclosed herein.

I claim:

1. Apparatus for detecting particles having at least a predetermined submicron size in a sample of gas containing such particles comprising:

means for detecting particles of a size substantially greater than said predetermined submicron size;

means for increasing the size of the particles having at least the predetermined submicron size in a sample of gas to said substantially greater size, said size increasing means comprising a bath of liquid and means defining a space over said bath, said bath and said space comprising means to saturate said gas sample with vapor from said liquid in said space;

means for condensing the vapor in the saturated sample around the particles in said sample having at least the predetermined submicron size to increase the size of said particles to said substantially greater size, wherein said space over said bath, said condensing means and said detecting means define a continuous flowpath for conveying a flow of said sample from said space to said detecting means;

means upstream of said space over said bath, with respect to the flow of said sample, for heating said sample, said heating means comprising a plurality of conduits connected in parallel extending through said bath of liquid, said conduits having outlet ends above the bath of liquid; and means for dividing a stream of a sample entering said plurality of conduits into a plurality of streams corresponding in number to the number of said conduits, wherein said dividing means comprises a plurality of channels connected with said conduits, and means for maintaining equal pressure in at least some of the plurality of said channels, said equal pressure maintaining means comprising at least one recombining channel connecting to one another two of the channels connecting with said conduits.

2. Apparatus for detecting particles having at least a predetermined submicron size in a sample of gas containing such particles comprising:

means for detecting particles of a size substantially greater than said predetermined submicron size;

means for increasing the size of the particles having at least the predetermined submicron size in the sample of gas to said substantially greater size, said size increasing means comprising a bath of liquid and means defining a space over said bath, said bath and said space comprising means to saturate said gas sample with vapor from said liquid in said space;

means for condensing the vapor in the saturated sample around the particles in said sample having at least the predetermined submicron size to increase the size of said particles to said substantially greater size, wherein said space over said bath, said condensing means and said detecting means define a continuous flowpath for conveying a flow of said sample from said space to said detecting means;

means upstream of said space over said bath, with respect to the flow of said sample, for heating said sample; and means for feeding a stream of the sample through said continuous flowpath in laminar flow.

3. Apparatus for detecting particles having at least a predetermined submicron size in a sample of gas containing such particles comprising:

means for detecting particles of a size substantially greater than said predetermined submicron size;

means for increasing the size of the particles having at least the predetermined submicron size in a sample of gas to said substantially greater size, said size increasing means comprising a bath of liquid and means defining a space over said bath, said bath and said space comprising means to saturate said gas sample with vapor from said liquid in said space;

means for condensing the vapor in the saturated sample around the particles in said sample having at least the predetermined submicron size to increase the size of said particles to said substantially greater size, wherein said space over said bath, said condensing means and said detecting means define a continuous flowpath for conveying a flow of said sample from said space to said detecting means; and means upstream of said space over said bath, with respect to the flow of said sample, for heating said sample, said heating means comprising a plurality of conduits connected in parallel extending through said bath of liquid, said conduits having outlet ends above the bath of liquid;

wherein said outlet ends outlet openings shaped and arranged to direct flow of said sample in a direction parallel to the surface of the bath of liquid.

4. Apparatus for detecting particles having at least a predetermined submicron size in a sample of gas containing such particles comprising:

means for detecting particles of a size substantially greater than said predetermined micron size;

means for increasing the size of the particles having at least the predetermined submicron size in a sample of gas to said substantially greater size, said size increasing means comprising a bath of liquid and means defining a space over said bath, said bath and said space comprising means to saturate said gas sample with vapor from said liquid in said space;

means for condensing the vapor in the saturated sample around the particles in said sample having at least the predetermined submicron size to increase the size of said particles to said substantially greater size, wherein said space over said bath, said condensing means and said detecting means define a continuous flowpath for conveying a flow of said sample from said space to said detecting means, and said means for condensing the vapor comprises a heat exchanger having a plurality of tubes connected in parallel, said tubes defining a portion of said continuous flowpath for said sample; and means upstream of said space over said bath, with respect to the flow of said sample, for heating said sample, wherein said tubes have funnel shaped inlet ends tapering in the direction of flow of the sample through said tubes.

5. The apparatus according to claim 4, wherein said tubes have inlet portions adjacent to and downstream of said funnel shaped inlet ends, said inlet portions having longitudinal axes inclined with respect to vertical, and said funnel shaped inlet ends are frustums of circular cones having oblique axes, said cones each having a side aligned with a side of the corresponding inlet portion.

6. A method for detecting particles having at least a predetermined submicron size in a sample of gas containing such particles, in which method such particles are substantially increased in size to a size detectable by a particle detector comprising:

heating the sample to a predetermined temperature;

passing the sample over a bath of a liquid maintained at said predetermined temperature to saturate said sample with vapor from said liquid;

cooling the saturated sample to condense the vapor into droplets around said particles to increase the size of the particles to the size detectable by the particle detector; and detecting the particles of the detectable size, wherein a rise in the predetermined temperature at which the bath of liquid is maintained results in a decrease in the size of particle which increases to the detectable size, and a lowering in the predetermined temperature at which the bath of liquid is maintained results in an increase in the size of particle which increases to the detectable size, the method further comprising maintaining the bath of liquid at aa relatively low temperature for a first portion of the sample to determine the number of particles having at least a first, relatively small size, and maintaining the bath of liquid at a relatively high temperature for a second portion of the sample equal in volume to the first portion of the sample to determine the number of particles having at least a second, relatively large size, and subtracting the number of particles of at least the second relatively large size from the number of particles of at least the first relatively small size to determine the number of particles in the sample in the range between the first and second size.

* * * * *